(12) United States Patent
Mitsuno et al.

(10) Patent No.: US 9,636,261 B2
(45) Date of Patent: May 2, 2017

(54) LEG GARMENT

(75) Inventors: Tamaki Mitsuno, Nagano (JP); Toshio Andou, Nara (JP); Ichirou Shinga, Nara (JP)

(73) Assignee: OKAMOTO CORPORATION, Nara (JP)

( * ) Notice: Subject to any disclaimer, the term of this patent is extended or adjusted under 35 U.S.C. 154(b) by 626 days.

(21) Appl. No.: 13/168,914

(22) Filed: Jun. 24, 2011

(65) Prior Publication Data
US 2011/0314591 A1    Dec. 29, 2011

(30) Foreign Application Priority Data

Jun. 25, 2010  (JP) ................ P2010-145323

(51) Int. Cl.
| | |
|---|---|
| A41B 9/00 | (2006.01) |
| A41B 9/02 | (2006.01) |
| A41B 9/04 | (2006.01) |
| A41B 11/00 | (2006.01) |
| A41B 11/02 | (2006.01) |

(Continued)

(52) U.S. Cl.
CPC ............ A61F 13/08 (2013.01); A61F 13/64 (2013.01); D04B 1/265 (2013.01)

(58) Field of Classification Search
CPC ................ A61F 13/08; A61F 13/64; A61F 2300/00089; A61F 2300/0016
USPC ....... 2/239, 241, 242, 22, 911, 61, 401, 404, 2/407, 409; 602/63, 65, 66; 66/182–188, 66/178 A
See application file for complete search history.

(56) References Cited

U.S. PATENT DOCUMENTS 4,216,547 A * 8/1980 Picchione .......... A41D 13/0015
2/22
4,862,523 A * 9/1989 Lipov ................. A41B 11/14
2/409
(Continued)

FOREIGN PATENT DOCUMENTS

| | | |
|---|---|---|
| DE | 34 16 253 | 11/1985 |
| EP | 1 323 397 | 7/2003 |

(Continued)

OTHER PUBLICATIONS

Office Action issued by JPO for JP 2010-145323, dispatched Feb. 4, 2014, 3 pgs.

(Continued)

*Primary Examiner* — Anna Kinsaul
*Assistant Examiner* — Cameron A Carter
(74) *Attorney, Agent, or Firm* — Squire Patton Boggs (US) LLP

(57) ABSTRACT

A leg garment according to the present invention includes a body portion covering at least an instep, a sole and an ankle of a leg. The leg garment includes a support strip exerting a tightening force larger than that of a portion of the leg garment around the support strip. The support strip is arranged in the shape of an inwardly-wound helix extending from the instep to the ankle through the sole. The support strip includes: a first tightening portion arranged so as to medially extend from the instep to the sole; and a second tightening portion arranged so as to extend obliquely upward from a lateral side to a medial side of a ventral ankle, the second tightening portion compressing the ventral ankle via a surface thereof.

7 Claims, 15 Drawing Sheets

(51) Int. Cl.
*A41D 13/00* (2006.01)
*A61F 13/08* (2006.01)
*A61F 13/64* (2006.01)
*D04B 1/26* (2006.01)

(56) References Cited

U.S. PATENT DOCUMENTS

| | | | | |
|---|---|---|---|---|
| 5,154,690 | A * | 10/1992 | Shiono | A61F 5/0102 602/21 |
| 5,263,923 | A * | 11/1993 | Fujimoto | A41D 13/0015 602/62 |
| 5,640,714 | A * | 6/1997 | Tanaka | A41B 11/00 2/22 |
| 5,898,948 | A * | 5/1999 | Kelly | A41B 11/00 2/239 |
| 6,012,177 | A * | 1/2000 | Cortinovis | A61F 13/08 2/239 |
| 6,286,151 | B1 * | 9/2001 | Lambertz | A41B 11/003 2/239 |
| 6,311,334 | B1 * | 11/2001 | Reinhardt | A61F 13/08 2/239 |
| 6,350,247 | B2 | 2/2002 | Bodenschatz | A61F 13/066 128/882 |
| 6,572,574 | B2 * | 6/2003 | Gardon-Mollard | D04B 9/52 602/62 |
| 6,729,164 | B2 * | 5/2004 | Shibata | 66/178 R |
| 6,805,681 | B2 * | 10/2004 | Yokoyama | 602/65 |
| 6,860,865 | B1 * | 3/2005 | Feldgiebel | A61F 13/085 602/60 |
| 7,192,411 | B2 * | 3/2007 | Gobet | A41B 11/003 2/239 |
| 7,434,423 | B1 * | 10/2008 | Reid, Jr. | A61F 13/08 66/178 A |
| 7,562,541 | B2 * | 7/2009 | Hermanson et al. | 66/186 |
| 7,757,518 | B2 * | 7/2010 | Sho et al. | 66/185 |
| D624,300 | S * | 9/2010 | Hollingsworth | D2/980 |
| 7,895,863 | B2 * | 3/2011 | Smith | A61F 13/08 66/172 E |
| 7,996,924 | B2 * | 8/2011 | Wright | A41D 13/0015 2/239 |
| 2002/0152773 | A1 * | 10/2002 | Shibata | A41B 11/02 66/69 |
| 2002/0169403 | A1 * | 11/2002 | Voskuilen | A61F 5/0111 602/27 |
| 2003/0230121 | A1 * | 12/2003 | Yokoyama | D04B 1/26 66/178 A |
| 2006/0085894 | A1 * | 4/2006 | Yakopson | D04B 1/265 2/239 |
| 2006/0247566 | A1 * | 11/2006 | Gobet | A41B 11/003 602/62 |
| 2008/0132822 | A1 * | 6/2008 | Hermanson | D04B 1/265 602/63 |
| 2008/0155731 | A1 * | 7/2008 | Kasahara | D04B 1/265 2/240 |
| 2009/0126081 | A1 * | 5/2009 | Lambertz | A61F 13/066 2/239 |
| 2009/0137938 | A1 * | 5/2009 | Parivash | A61F 13/08 602/63 |
| 2009/0165190 | A1 * | 7/2009 | Araki | A61F 13/064 2/240 |
| 2009/0178179 | A1 * | 7/2009 | Liu | A41B 11/00 2/239 |
| 2009/0276939 | A1 * | 11/2009 | Sho | A41B 11/02 2/239 |
| 2009/0288451 | A1 * | 11/2009 | Yokoyama | A41B 11/004 66/185 |
| 2011/0107501 | A1 * | 5/2011 | Kawahara | A41B 11/02 2/239 |
| 2011/0196416 | A1 * | 8/2011 | Lambertz | A61F 13/08 606/201 |

FOREIGN PATENT DOCUMENTS

| | | |
|---|---|---|
| JP | H10-310903 | 11/1998 |
| JP | 3091572 | 11/2002 |
| JP | 2005163209 A | 6/2005 |
| JP | 2006-312789 | 11/2006 |
| JP | 2007-138348 | 6/2007 |
| JP | 2006-219805 | 8/2008 |
| JP | 2008-266802 | 11/2008 |
| JP | 2009-275300 | 11/2009 |
| WO | WO 2007/147980 | 12/2007 |

OTHER PUBLICATIONS

Office Action from the State Intellectual Property Office of P.R.C. for application No. CN 201110180113.0, dispatched Jan. 3, 2014, 8 pgs.
Office Action issued by JPO for JP 2010-145323, dispatched Jul. 29, 2014, 4 pgs.
European Search Report for EP11171278.2, dated Dec. 4, 2012, 6 pgs.
Office Action issued by State Intellectual Property Office of China for Application No. CN 201110180113.0, dispatched Jul. 30, 2014.

* cited by examiner (A)

(B)

(C)

LEG GARMENT

BACKGROUND OF THE INVENTION

Field of the Invention

The present invention relates to a leg garment including a support strip in a tubular body portion, the support strip exerting a tightening force larger than that of a portion of the leg garment around the support strip.

Related Background Art

In recent years, an increasing number of people perceive swelling of their lower legs. Accordingly, there is a demand for getting rid of swelling with a view to a trimming effect. A lower leg is a body part that is less subject to the effect of breathing, and thus, suffers no harm even when a certain degree of compressing force is imposed thereon. Therefore, in order to suppress lower leg swelling, compression socks that compress lower legs of a wearer by means of a circumferential force (circumferential stress or hoop tension) from the circumference to the deep part of the respective lower leg, which is generated as a result of tightening the lower leg, have been developed to reduce the amount of swelling in the lower leg.

Japanese Patent Laid-Open No. 2008-266802 discloses a leg garment including a helical support strip formed therein. The support strip in this leg garment has the shape of an outwardly-wound helix extending from a lateral malleolus to a lower end of a posterior surface of a knee knot via a posterior ankle. Formation of such support strip provides an effect on the skeleton of a lower leg to enhance the mobility of the bones, thereby preventing, e.g., swelling, heaviness or tiredness of the leg.

Japanese Patent Laid-Open No. 2006-219805 discloses a sock including a plurality of compression portions extending obliquely upward, the compression portions being arranged so as to be vertically spaced from one another. In this sock, each compression portion is formed along the direction of the flow of lymph in an attempt to provide stimulatory and massaging effects along the flow of lymph by means of the effect of pressing a skin surface of a lower leg via the compression portion.

Japanese Utility Model Registration No. 3091572 discloses a supporter formed in a tubular shape, in which elastic fabric portions and intermediate fabric portions (non-elastic fabric portions) are alternately arranged in a circumferential direction of a leg, and the supporter is put on a calf by twisting one of openings of the supporter relative to the other opening. Japanese Patent Laid-Open No. 10-310903 discloses a sock whose compression force is gradually changed in a vertical direction to promote blood flow.

SUMMARY OF THE INVENTION

In the leg garment described in Japanese Patent Laid-Open No. 2008-266802, the support strip is arranged to obliquely extend across a shin (front surface of a shank) from a lower end of a shin bone to a position corresponding to one-fourth to a half of the entire length of the shin bone. At this position in the shin, a great saphenous vein 131 and a saphenous nerve 132 are superficially present. Formation of a support strip so as to extend across such vein and nerve at the shin impede return of venous blood and thus, disturbs blood circulation, causing a problem in that swelling cannot be removed.

Where a support strip is formed in the shape of an outwardly-wound helix, it is difficult to effectively arrange the support strip so as not to extend across the great saphenous vein 131 and the saphenous nerve 132, disabling effective swelling removal.

Where a lower leg of a wearer is compressed by an excessive circumferential force that makes the wearer find it too tight, blood circulation may be suppressed, resulting in cooling in the toes. If a further increased circumference force is applied, the wearer may have a pain during wearing or deformation of the subcutaneous tissue at the corresponding region of the leg after wearing.

For example, for the conventional art described in Japanese Patent Laid-Open No. 2008-266802, it is described that a pressure value of a portion (point P) of a leg support strip portion that provides a highest pressure is preferably 1.1 kPa to 5.0 kPa. However, such high pressure value can be considered to produce excessively strong compression on the body part.

Furthermore, the conventional art described in Japanese Patent Laid-Open No. 2006-219805 and the conventional art described in Japanese Utility Model Registration No. 3091572 do not take parts such as a part from toes to a malleolus (foot part) and a sole into consideration, causing a problem in that a plantar vein, which easily swell, cannot be compressed. Furthermore, such conventional art results in an improper pressure balance for the part from a foot to a calf, and thus, cannot favorable tightening as a compression sock (leg garment), disabling reduction of load on the wearer's body, causing a problem in that swelling cannot healthily be reduced.

In the conventional art described in Japanese Patent Laid-Open No. 10-310903, a lower leg is tightened by hoop tensions in respective courses, which tighten the lower leg from all the directions, and thus, a feeling of excessively tightness is given to a wearer, which may cause the wearer to have a discomfort feeling.

The present invention has been made to solve such problems, and an object of the present invention is to provide a leg garment capable of promoting blood circulation to remove swelling while preventing a wearer from having a discomfort feeling because of excessive tightness and providing a moderate pressure sensation (feeling of moderate tightness), as well as suppressing impediments for blood circulation to maintain a heat-retention effect.

As a result of diligent study to achieve the above object, the present inventors discovered that: arranging a support strip so as to avoid a part in which a great saphenous vein, a saphenous nerve and a lateral sural cutaneous nerve are superficially present enables effective removal of swelling without disturbing blood circulation; and a large correction effect can be provided by obliquely laying a support strip on a ventral ankle, whose shape varies most largely in a lower leg and whose volumetric change rate is high, to compress such part. The term "ventral" means a front side of a wearer (side on which a face of a wearer is present).

The present invention provides a leg garment including a body portion covering at least an instep, a sole and an ankle of a leg, the leg garment including a support strip arranged in the shape of an inwardly-wound helix extending from the instep to the ankle through the sole, the support strip exerting a tightening force larger than that of a portion of the leg garment around the support strip, wherein the support strip includes: a first tightening portion arranged so as to medially extend from the instep to the sole; and a second tightening portion arranged so as to extend obliquely upward from a lateral side to a medial side of a ventral ankle, the second tightening portion compressing the ventral ankle via a surface thereof.

According to such a leg garment, a support strip is formed in the shape of an inwardly-wound helix, the support strip exerting a tightening force larger than that of a part of the leg garment around the support strip, facilitating easy setting of the strip so as to avoid a part in which a great saphenous vein, a saphenous nerve and a lateral sural cutaneous nerve are superficially present. Furthermore, formation of a helical support strip enables hoop tension to be relieved to produce moderate tightening, and thus, enables reduction of a feeling of excessive tightness a wearer may have. Consequently, it is possible to prevent an unnecessary load from being imposed on the wearer's body. Furthermore, setting of the support strip so as to avoid a part in which a great saphenous vein, a saphenous nerve and a lateral sural cutaneous nerve are superficially present enables provision of a favorable support strip that does not disturb return of venous blood and lymph to the heart.

Furthermore, the support strip includes a first tightening portion medially extending from an instep to a sole. An instep is a body part that less makes the wearer have a feeling of excessive tightness even where it is firmly tightened, compared to the other body parts. Accordingly, formation of a support strip continuously extending on the other body parts through an instep makes other body parts spaced via the instep move in conjunction with each other, enabling effective exertion of a tightening force. Furthermore, since the support strip is arranged on a sole (arch), which is a body part that easily swells, the support strip compresses a plantar vein, enhancing blood circulation. For example, it is preferable to employ tuck knitting for a portion of the first tightening portion corresponding to a sole to provide an increased tightening force compared to a portion of the leg garment around that portion. Here, "instep" refers to a part corresponding to cuneiform bones.

Furthermore, the support strip includes a second tightening portion arranged so as to extend obliquely upward from a lateral side to a medial side of a ventral ankle, the second tightening portion compressing the ventral ankle via a surface thereof. Consequently, arrangement of the second tightening portion obliquely relative to a vertical direction of the wearer's body prevents compression caused by hoop tension, enabling the ventral ankle, which is a soft tissue and susceptible to load, to be compressed via a surface of the second tightening portion. More specifically, prevention of occurrence of wrinkles, which easily occur at a ventral ankle, and compression of the ventral ankle via the surface prevents local compression occurring as a result of the fabrics overlapping, enabling reduction of damage of not only skin tissues but also muscle cells in a part deeper than the skin, and thus, enabling prevention of local compression on the great saphenous vein and the saphenous nerves superficially present in the ventral ankle. Since the second tightening portion is formed so as to extend through the ventral ankle, a part of the support strip extending across the great saphenous vein, the saphenous nerve and the lateral sural cutaneous nerve can be minimized, enabling setting of a favorable support strip.

Furthermore, it is preferable that: the body portion be formed so as to cover at least a part up to a part of the leg above the ankle; and the support strip include a third tightening portion arranged so as to cover a muscle-tendon junction connecting an Achilles tendon and a triceps surae muscle, a lower end side of the third tightening portion being continuous with an upper end side of the second tightening portion. Consequently, a calf muscle is lifted up by the third tightening portion, enabling enhancement of return of blood and lymph to the heart, and thus, enabling swelling to be removed effectively.

Furthermore, it is preferable that: the body portion be formed so as to cover at least a part of the leg up to a lower leg; and the support strip include a fourth tightening portion arranged so as to extend obliquely upward from an external side of the lower leg to a ventral side of the lower leg to reach a ventral side of a lower end of a knee cap. Consequently, the support strip can be formed so as to avoid the part in which the great saphenous vein, the saphenous nerve and the lateral sural cutaneous nerve are superficially present, the part being located medial to the center of the body of the wearer relative to a shin bone, enabling return of venous blood and lymph to the heart to be prevented from being disturbed, as well as compressing a part of the wearer's body from a ventral side of a lower leg from a lateral side of the lower leg to promote blood circulation.

Furthermore, it is preferable that: the body portion be formed so as to cover at least a part of the leg from a position corresponding to a body of a metatarsal bone to a position corresponding to the lower end of the knee cap; the support strip be formed so as to continuously extend from a position in a plantar part corresponding to a body of a third or fourth metatarsal bone to a position corresponding to the ventral side of the lower end of the knee cap; and values of pressures exerted by the body portion satisfy expression (1) below:

$$\text{foot circumference:minimum lower leg circumference:maximum lower leg circumference}=2.2:1.6:1.0 \quad (1).$$

Consequently, the support strip can be formed so as to continuously extend for both the wearer's body parts of the foot and the lower leg, enabling provision of a favorable pressure balance for the foot, the ankle and the lower leg. A "foot" refers to a part from toes to a malleolus, and a lower leg refers to a part from a malleolus to a part just below a knee. Also, a foot circumference refers to a part extending through an arch and cuneiform bones. A minimum lower leg circumference refers to a part whose circumference is the smallest in the lower leg (part corresponding to an ankle). A maximum lower leg circumference refers to a part whose circumference is the largest in the lower leg (part corresponding to a calf).

DESCRIPTION OF THE PREFERRED EMBODIMENTS

Figure 1:
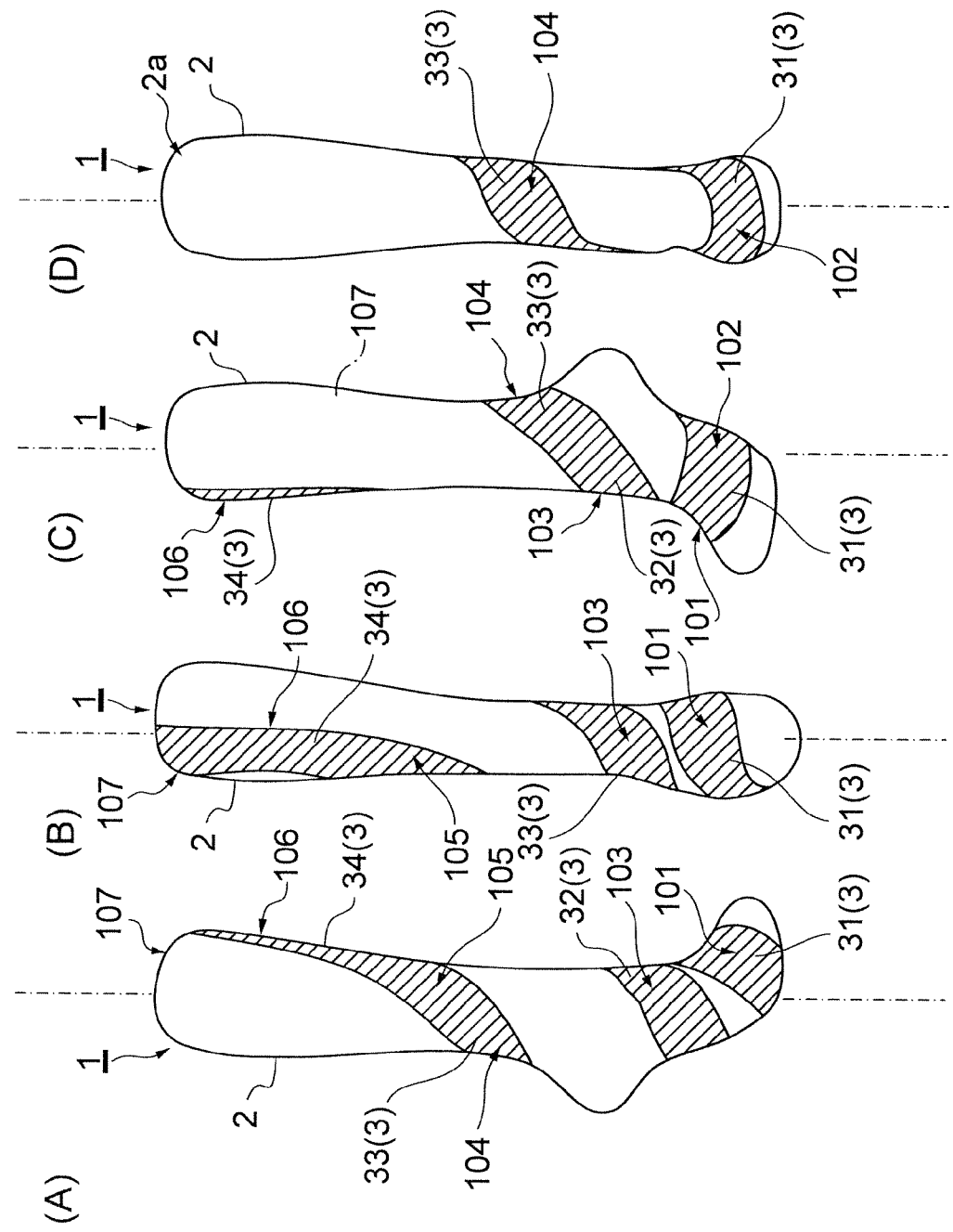
FIGS. 1A to 1D are diagrams each illustrating a compression sock (for a right leg) according to an embodiment of the present invention.

Hereinafter, a preferred embodiment of the present invention will be described in details with reference to the drawings. Here, components that are identical or correspond to each other in the respective drawings are provided with a same reference numeral. In the present embodiment, a description will be given in terms of a compression sock (leg garment).

Figure 2:
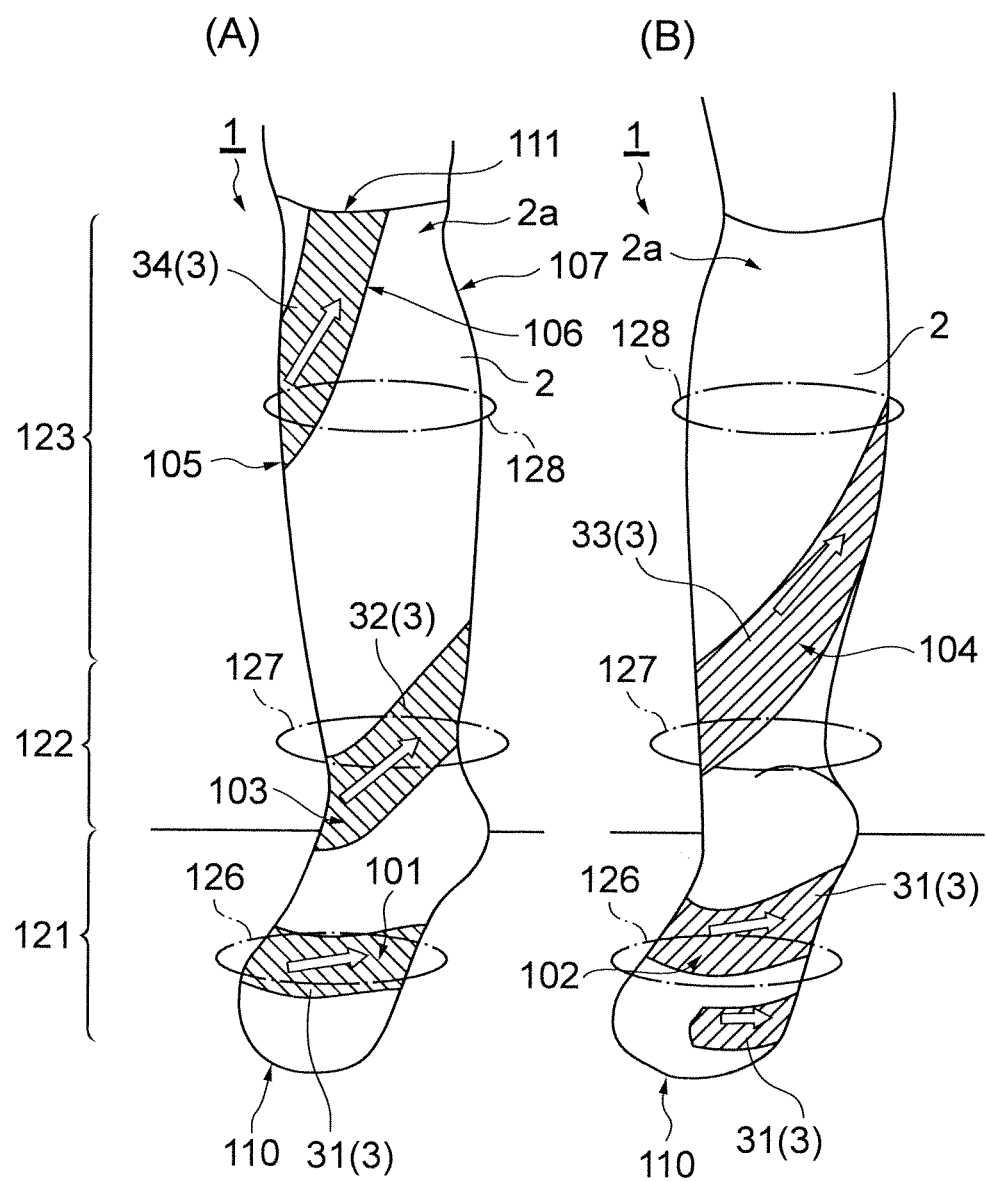
FIGS. 2A and 2B are other diagrams each illustrating the compression sock (for a right leg) according to the embodiment of the present invention.

FIGS. 1(A) to 1(D) and 2(A) and 2(B) are diagrams each illustrating a compression sock (for a right leg) according to an embodiment of the present invention. FIG. 1(A) is an outer side view. FIG. 1(B) is a front view. FIG. 1(C) is an inner side view. FIG. 1(D) is a back view. Also, FIG. 2(A) is a front view. FIG. 2(B) is a back view.

The compression sock 1 (helical compression sock) illustrated in FIGS. 1(A) to 1(D) and FIGS. 2(A) and 2(B) is a sock including a support strip 3 formed in a tubular body portion 2, the support strip 3 exerting a tightening force larger than that of a part of the compression sock 1 around the support strip 3. In the compression sock 1, the tightening force exerted by the support strip 3 compresses a lower leg and a foot, enhancing blood circulation to prevent swelling. Furthermore, the compression sock 1 provides the trimming effect of making a leg of a wearer look slim.

The body portion 2 is formed from toes 110 to a position reaching a lower end 111 of a knee cap. The body portion 2 is made to include a structure covering a lower leg 123 and a foot 121 in their entireties. In other words, the body portion 2 is formed so as to cover toes, an instep, a sole, an ankle, a heel, a shin, a calf and a lower end of a knee cap of a leg. A fabric for the body portion 2 is formed by a stretchable knitted fabric using, for example, flat knitting.

The body portion 2 is formed so as to have a length larger than that of an ordinary knee-high sock. An upper end of the body portion 2 is preferably formed so as to slightly cover the lower end 111 of the knee cap when the compression sock 1 is worn. A knee is a part that is highly sensitive for activating blood circulation, and thus, heat retention is provided by covering a knee, enabling activation of blood circulation. Even if only the lower end 111 of the knee is covered, blood circulation of the wearer can be activated.

Furthermore, a cuff 2a provided at an upper end of the body portion 2 includes a base fabric alone and produces gentle compression. Consequently, a local pressure can be prevented from being generated at the cuff 2a.

Next, a pressure sensation for a circumference force on each of a lower leg 123 and a foot 121 will be described. A pressure sensation refers to a sensation of a person to feel pressure when he/she wear a leg garment. A rule for a pressure sensation that gives the wearer a feeling of moderateness is achieved where average pressures of circumference forces satisfy the following expression (2):

Foot circumference:minimum lower leg circumference:maximum lower leg circumference:below-the-knee circumference=2.2:1.6:1.0:1.0    (2).

Pressures generated at the ratio indicated by expression (2) make more people have a feeling of moderateness. In other words, the body portion 2 of the compression sock 1 is preferably formed so that the pressure balance of thereof satisfies expression (1), that is, foot circumference 126:lower leg minimum circumference 127:lower leg maximum circumference 128=2.2:1.6:1.0    (1).

According to the inventors' study, a limit pressure for a wearer of a compression sock to wear the compression sock comfortably is around 20 hPa for a lower leg. (The limit pressure was measured using a closing pressure measurement system by a hydrostatic pressure balance method. This measurement method is described in details in Non-Patent Document 1 (Mitsuno, Tamaki, et al, Journal of the Japan Research Association for Textile End-Use, Vol. 32, No. 8, separate reprint, "Studies on the Clothing Pressure (Part 1). Measurements by a Hydrostatic Pressure-Balanced Method", The Japan Research Association for Textile End-Use, 1991, p.p. 34 to 39), and Non-Patent Document 2 (Mitsuno, Tamaki, et al., Journal of the Japan Research Association for Textile End-Use, Vol. 32, No. 8, separate reprint, "Studies on the Clothing Pressure (Part 2). Measurements by a Hydrostatic Pressure-Balanced Method", The Japan Research Association for Textile End-Use, 1991, p.p. 40 to 44).

For example, a pressure when only one aspect of a body is tightened using a rubber band (tightening portion material) with a width of 2.5 cm is around 44 hPa at a foot, around 32 hPa at an ankle and around 20 hPa at a lower leg. However, when the area covered by the rubber band (tightening portion material) increases, the pressure exceeds the aforementioned limit pressure (20 hPa for a lower leg) unless the value of the pressure resulting from compression produced by the tightening portion material is decreased. The rubber band used here is one with a typical stretchable material such as exhibiting stress (kgf/2.5 cm)-strain (mm) characteristics of a strain of 0 (mm) for a stress of 0 (kgf/2.5 cm), a strain of 8.3 (mm) for a stress of 240 (kgf/2.5 cm), a strain of 15.0 (mm) for a stress of 320 (kgf/2.5 cm), a strain of 25.1 (mm) for a stress of 360 (kgf/2.5 cm), a strain of 33.3 (mm) for a stress of 390 (kgf/2.5 cm), a strain of 41.7 (mm) for a stress of 460 (kgf/2.5 cm), and a strain of 50.0 (mm) for a stress of 580 (kgf/2.5 cm) (Test environment: 20° C., relative humidity of 65%, tensile rate: 50 mm/min, grip-to-grip distance: 10 cm, Shimadzu Corporation's AUTOGRAPH S-100 used).

Although there is no problem in tightening with a pressure up to around 32 hPa, as the ankle is tightened more firmly, the volume of the entire ankle is decreased; however, tightening of the ankle results in a significant increase in the volume of the foot. For example, when wearing a pump, it is not a good idea to tighten the ankle too firmly. Furthermore, although there is a significant correlation between pressure sensation and pressure value, as the area covered by the tightening portion material increases, the pressure value decrease, and the pressure sensation transitions to depend on a correlation with "the product of the pressure value and the covered area". Where the entire ankle (with a breadth of around 7.5 cm) is tightened, a pressure of around 13 to 15 hPa can be considered to be a limit value for a wearer to have a feeling of moderateness.

Therefore, reconsidering expression (1), the pressure balance ratio for a wearer to comfortably wear a compression sock preferably satisfies expression (3).

Foot circumference 126:minimum lower leg circumference 127:maximum lower leg circumference 128=18 hPa:13 hPa:8 hPa (3)

However, taking individual differences such as the degree of muscle development, taste, etc., expression (4) can be considered as a tolerable range of pressure for a wearer to have a feeling of moderateness.

Foot circumference 126:minimum lower leg circumference 127:maximum lower leg circumference 128=18 hPa to 40 hPa:13 hPa to 26 hPa:8 hPa to 20 hPa (4).

An average pressure applied to each of the foot circumference 126, the minimum lower leg circumference 127 and the maximum lower leg circumference 128 in the body portion 2 is made to fall within the range indicated by expression (4). However, uniformly compressing horizontal circumferences of the area from the toes to the knee in such a manner that the applied pressure is decreased gradually from the toes to the knee can be considered to a cause of disturbance of blood circulation to the toes.

Therefore, in the compression sock 1 according to the present embodiment, there is a difference in compression strength in a same circumference. A compression strength represents the degree of the strength of a force of the body portion 2 of the compression sock 1 compressing a body part of a wearer. Parts whose volumes are significantly reduced as a result of compression are a ventral ankle 103 and an arch 102. Therefore, in the compression sock 1, pressure is applied to the ventral ankle 103 and the arch 102 by means of not a tightening portion material arranged on a same circumference but the support strip (compression band) 3 arranged in the shape of a helix.

Next, the support strip 3 will be described. The support strip 3 is a compression band having a large tightening force compared to that of the surrounding fabric. The support strip 3 is formed so as to moderately compress a body part in contact with the support strip 3 when the compression sock 1 is worn.

The support strip 3 is a belt-like portion with its tightening force increased by suppressing its stretch properties, and provided integrally with the fabric of the body portion 2. It is preferable that the belt-like portion have a width of, for example, around 3.5 to 5.0 cm in a state in which no pressure is generated.

Figure 3:
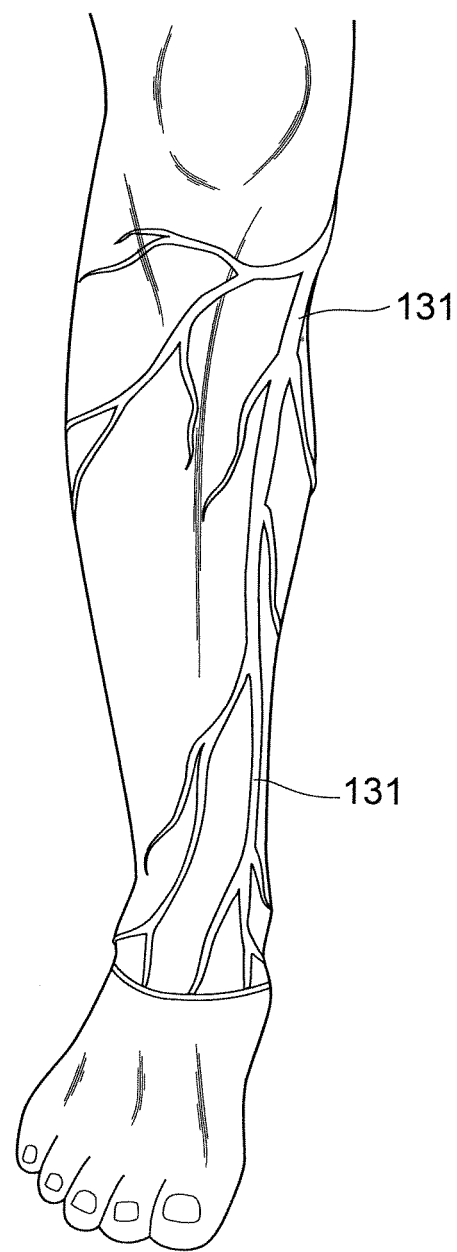
FIG. 3 is a diagram of a lower leg (right leg) viewed from a ventral side (front side), which illustrates a position of a great saphenous vein.
Figure 4:
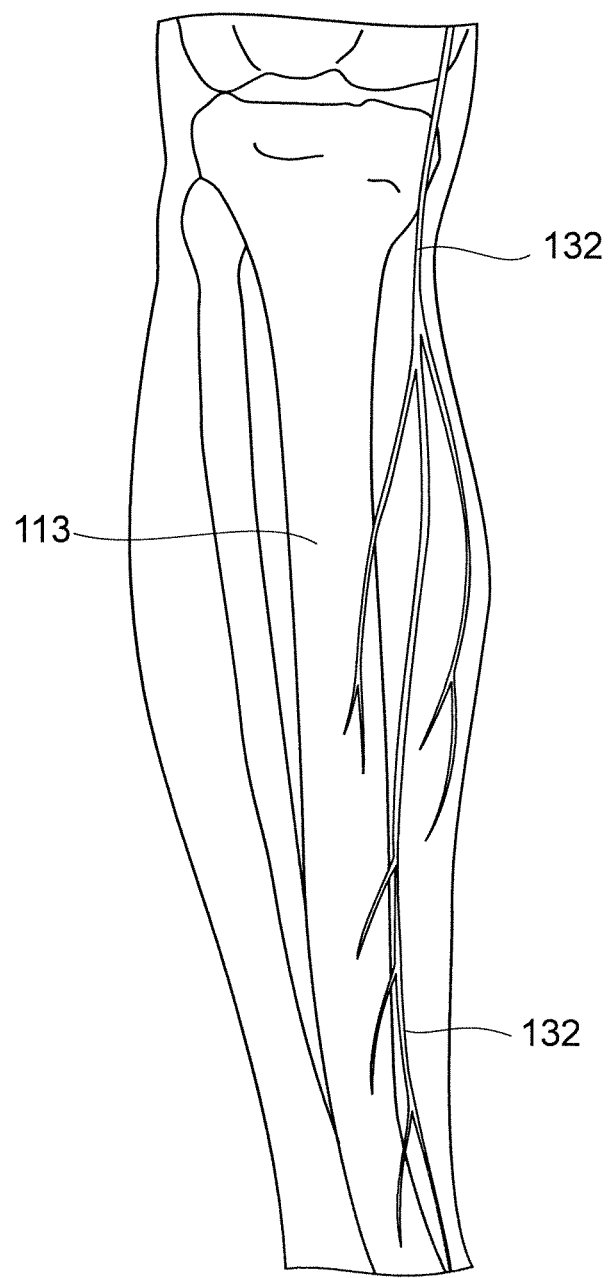
FIG. 4 is a diagram illustrating a lower leg (right leg) viewed from a ventral side (front side), which illustrates a position of a saphenous nerve.
Figure 5:
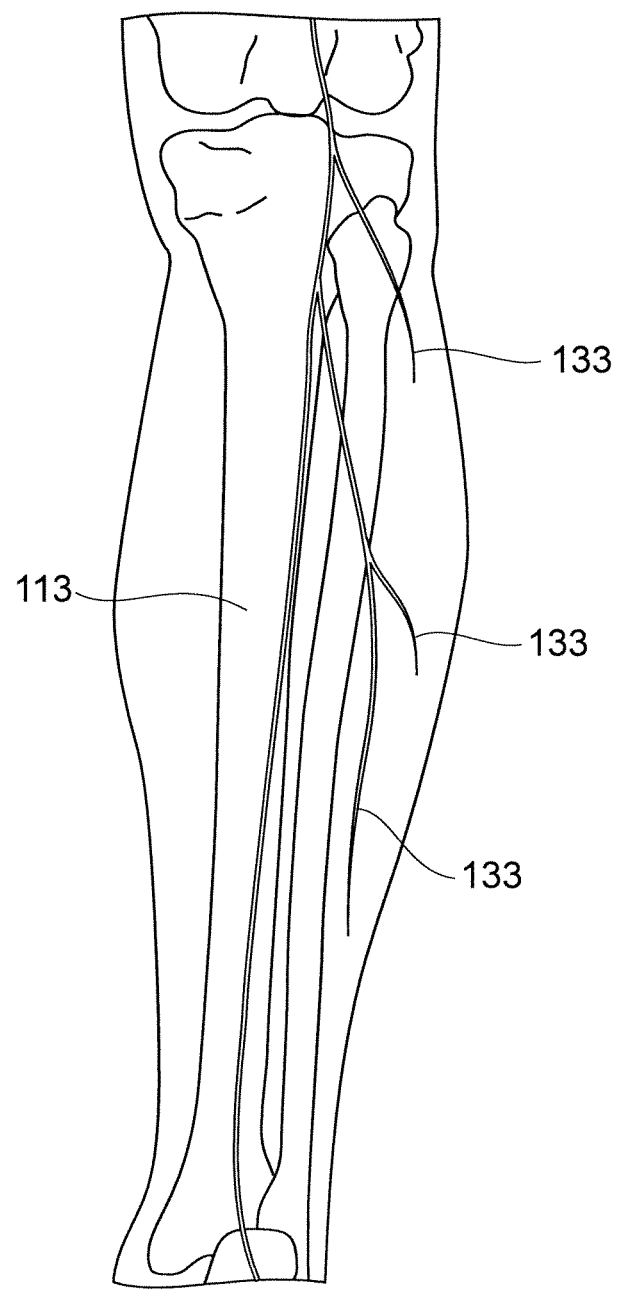
FIG. 5 is a diagram of a lower leg (right leg) viewed from a dorsal side, which illustrates a position of a lateral sural cutaneous nerve.

It is preferable that the support strip 3 be arranged so as to meet the following conditions. For a first condition, the support strip 3 is arranged so as to cover body parts that not directly compress the great saphenous vein 131 (see FIG. 3), the saphenous nerve 132 (see FIG. 4) and a lateral sural cutaneous nerve 133 (see FIG. 5), and formed in the shape of a helix.

For a second condition, the support strip 3 is arranged so as to compress the ventral ankle 103 via a surface thereof. Since the great saphenous vein 131 and the saphenous nerve 132 are superficially present also in the ventral ankle 103, arrangement of the support strip 3 on the ventral ankle 103 results in direct compression of the great saphenous vein 131 and the saphenous nerve 132. Therefore, it is preferable to produce compression via a surface of the support strip 3 to prevent the support strip 3 from biting into the body part in the ventral ankle 103. In particular, in a state in which a wearer stands upright at rest, extra fabric appearing on the ventral ankle 103 is folded so as to overlap each other and bit into the body part. Accordingly, it is desirable to prevent occurrence of wrinkles on the ventral ankle 103 to the possible extent.

Figure 6:
FIG. 6 is a diagram of a lower leg (left leg) viewed from a dorsal side, which illustrates a position of a small saphenous vein.

For a third condition, the support strip 3 is arranged so as not to extend across the great saphenous vein 131 and the saphenous nerve 132, which are superficially present on a medial side (center side of the body) of a shin bone 113, a small saphenous vein 134 (see FIG. 6) penetrating into the muscle belly of the calf muscle, and the lateral sural cutaneous nerve 133 to the possible extent.

For a fourth condition, the support strip 3 is arranged so as to draw a helix from the toes to the knee, forming a helix inwardly wound relative to the axis direction of the leg.

Figure 7:
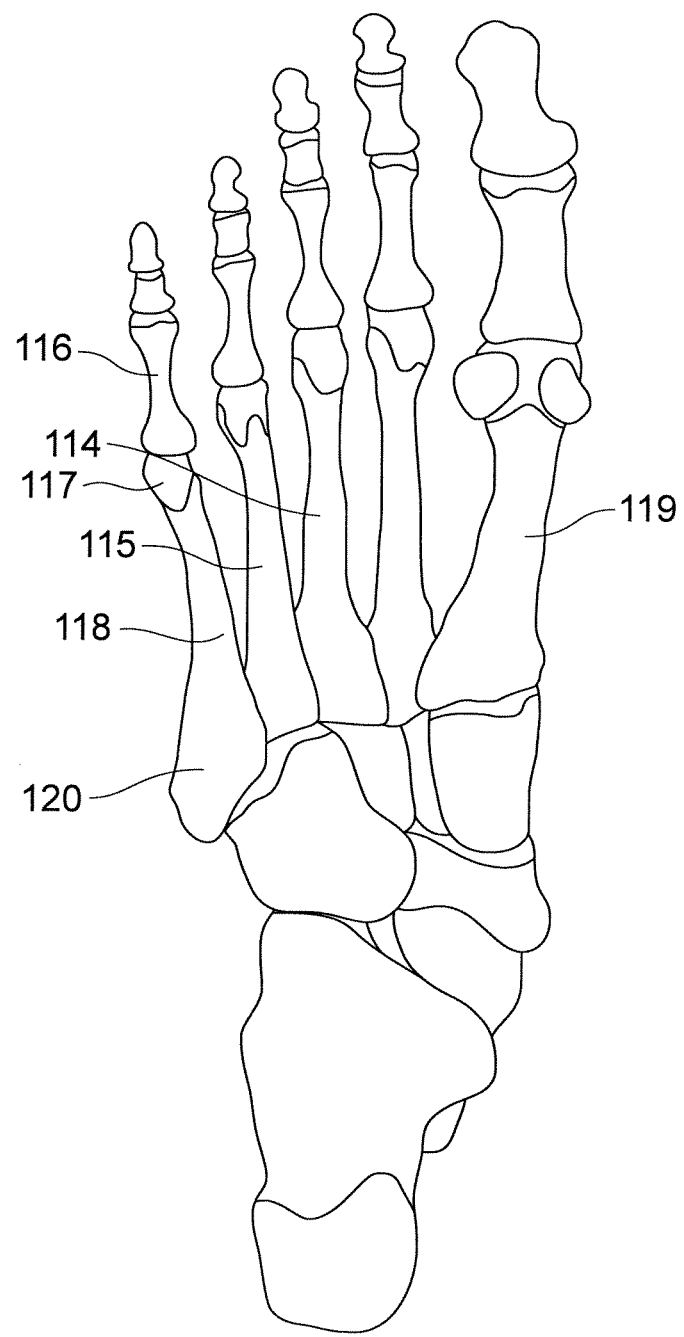
FIG. 7 is a diagram of a right leg viewed from a plantar part, which illustrates a metatarsal bone.
Figure 8:
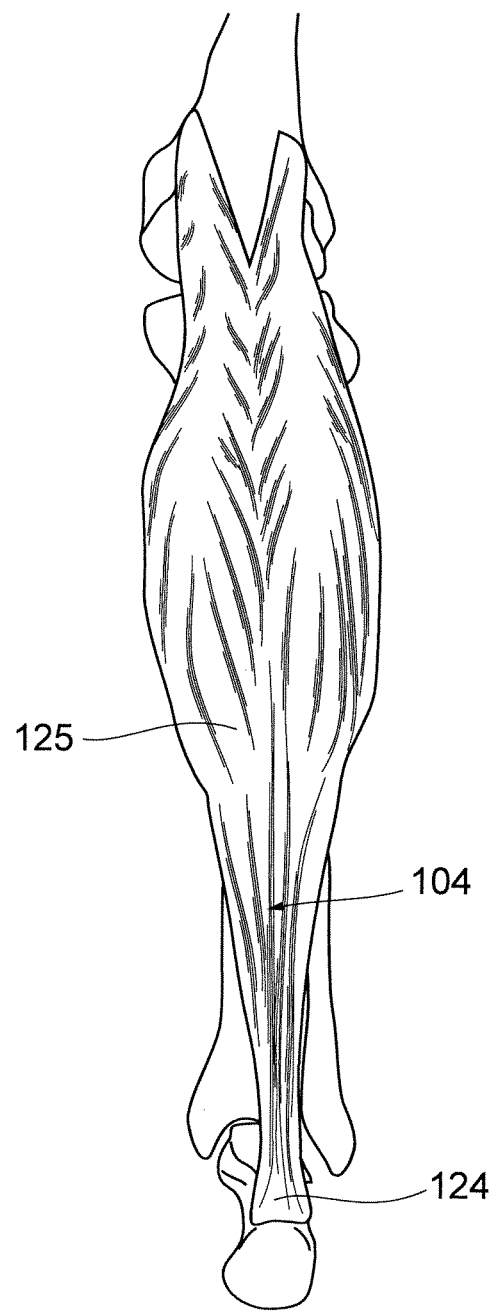
FIG. 8 is a diagram of a lower leg (left leg) viewed from a dorsal side, which illustrates a position of a muscle-tendon junction connecting an Achilles tendon and a triceps surae muscle.

More specifically, the support strip 3 laterally extends from a position in a plantar part corresponding to a body 114 or 115 of a third or fourth metatarsal bone (see FIG. 7) to an instep 101. The support strip 3 includes a first tightening portion 31 arranged so as to medially extend from the instep 101 to the sole 102, a second tightening portion 32 formed so as to be continuous with the first tightening portion 31 and arranged so as to extend obliquely upward from a lateral side to a medial side of the ventral ankle 103, a third tightening portion 33 formed so as to be continuous with the second tightening portion 32 and arranged so as to cover a muscle-tendon junction 104 (see FIG. 8) connecting an Achilles tendon 124 and a triceps surae muscle 125, and a fourth tightening portion 34 formed so as to be continuous with the third tightening portion 33 and arranged so as to extend obliquely upward from a lateral side 105 of the lower leg to a ventral side 106 of the lower leg to reach a ventral side of a lower end of a knee cap 111. As a result of forming the tightening portions 31 to 34 so as to be continuous with one another, the support strip 3 forms an inwardly-wound helix.

More specifically, the first tightening portion 31 starts from the position in the plantar part corresponding to the body of the third or fourth metatarsal bone 114 or 115. The first tightening portion 31 is wound up in the lateral direction, heads toward the ventral side while covering a proximal phalange 116 of the fifth toe and a head 117 and a body 118 of a fifth metatarsal bone, passes through a position corresponding to a body 119 of a first metatarsal bone and extends to the sole 102. The first tightening portion 31 heads toward the ventral side while covering the arch 102 and a tuberosity 120 of the fifth metatarsal bone, and is continuous with the second tightening portion 32. The instep 101 in which the nerves and blood are protected by the bones is a part that can be compressed by the first tightening portion 31. Also, the plantar vein (sole), which easily swells, is compressed by the first tightening portion 31.

The second tightening portion 32 is formed so as to extend obliquely upward from the lateral side to the ventral side to cover the ventral ankle 103 and is continuous with the third tightening portion 33. The ventral ankle 103, which is soft compared to the other body parts and susceptible to damage, is compressed by the second tightening portion 32 via a surface thereof. The second tightening portion 32 is configured to be resistant to wrinkling.

The third tightening portion 33 extends through an upper part of the medial malleolus while being wound obliquely upward on an upper part of the Achilles tendon 124. The third tightening portion 33 is formed so as to extend obliquely upward from the medial side to the lateral side on an upper part of the dorsal ankle (lower part of the dorsal lower leg), and cover the muscle-tendon junction 104 connecting the Achilles tendon 124 and the triceps surae muscle 125, and is continuous with the fourth tightening portion 34. The calf muscles 125, which easily swells, is compressed by the third tightening portion and pulled upward. A triceps surae muscle is a name of a body part that is a combination of the calf muscles 125 and the soleus muscle.

The fourth tightening portion 34 is arranged obliquely upward from the lateral side 105 of the lower leg to the ventral side 106 of the lower leg and extends to the ventral side of the lower end of the knee cap 111. The fourth tightening portion 34 is formed so as to cover the part from the lateral side 105 of the lower leg to the ventral side 106 of the lower leg, and the ventral side of the lower end of the knee cap 111. In other words, the fourth tightening portion 34 extends obliquely upward across a center of the lateral side of the body of the fibula (in the order of the muscle belly of the short peroneal muscle, the muscle belly of the long peroneal muscle and the muscle belly of the anterior shin bone muscle), and wound up toward the ventral knee cap. The fourth tightening portion 34 is pulled up along movement of the calf muscle 125, pulls up the third tightening portion 33, with which the fourth tightening portion 34 is continuous downwardly, enabling the other body parts to move in conjunction with movement of the calf muscle 125. Furthermore, the fourth tightening portion 34 is not arranged on a medial side 107 of the lower leg in which the great saphenous vein 131 and the saphenous nerve 132 are superficially present in order not to compress the great saphenous vein 131 and the saphenous nerve 132.

Since the support strip 3 is arranged corresponding to the positions of bones and muscles of a wearer, body parts that are symmetrical between the left and right legs are compressed. The tightening portions 31 to 34 may have a same width or may also have different arbitrary widths according to the respective compressed body parts. For example, provision of different arbitrary widths of the tightening portions 31 to 34 enables adjustment of tightening forces for the respective parts.

Figure 9:
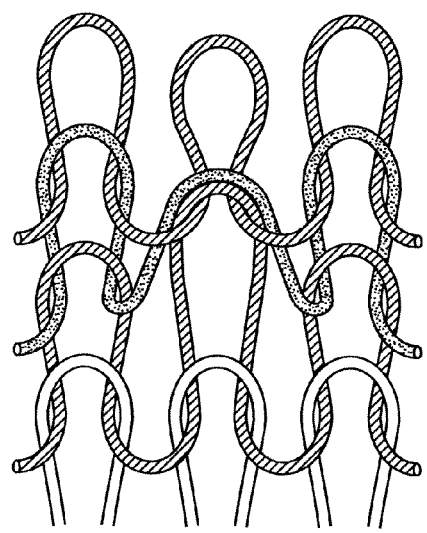
FIG. 9 is a diagram illustrating a tuck knitting texture.

The tightening portions 31 to 34 included in the support strip 3 are provided with a texture different from their surrounding portion, have an increased tightening force, and are formed integrally with the body portion 2. FIG. 9 is a diagram illustrating a tuck-knitting texture. The tightening portions 31 to 34 may be provided with different tightening forces by forming tuck-knitting portions in the support strip 3 and changing the proportion of the tuck-knitting portion for the respective tightening portions. Since the tuck-knitting portions can suppress extension in the lateral direction (wale direction), the tightening force can be adjusted by increasing the amount of the tuck knitting portion per unit area. Alternatively, the tightening force may be adjusted within the areas of the respective tightening portions 31 to 34 by changing the proportion of the tuck knitting portion. In the second tightening portion 32, tuck texture is distributed, forming a configuration that is resistant to wrinkling compared to the other portions. The support strip may be formed using, for example, a patch that is a separate member.

Next, an operation of the compression sock 1 will be described. The compression sock 1 is in close contact with a body part of a wear when it is worn and adequately compresses the body part. The compression sock 1 assists the flow of blood and lymph from the toes to the lower leg and thigh by means of varied compression forces provided by the helical support strip 3. In general, swelling in the legs increases when a person continues to stand or sit without changing the posture. However, the compression sock 1 provides the effect of reducing swelling even in a state in which the wearer has almost no movements. Furthermore, the compression sock 1 provides an increased swelling reduction effect when the wearer moves.

Next, an operation of the compression sock 1 when a wearer moves will be described in details. For example, when a wearer stands up, the calf muscle 125 is tensed, and thus, the third tightening portion 33 and the fourth tightening portion 34 are pulled. Upon the tightening portions 33 and 34 being pulled, the second tightening portion 32, which compresses the ventral ankle 103, is pulled following the tightening portions 33 and 34. Subsequently, the first tightening portion 31, which is continuous with the second tightening portion 32, is pulled, and the arch 102 is thereby compressed, too.

Alternatively, when a wearer sits down, the calf muscle 125 is relaxed. Then, the tensions of the second tightening portion 32, which is in contact with the ventral ankle, and the third tightening portion 33, which is in contact with the arch, are reduced, resulting in the support strip 3 being loosened.

Meanwhile, when a wearer bends and stretches his/her ankles, the third tightening portion 33 and the fourth tightening portion 34, which compress the calf muscle, expand and contract in response to movements of the ankle, and movements of the calf muscle 125 promotes muscle pumping for enhancing the flow of blood. In other words, when a body part that is in contact with any of the tightening portions 31 to 34 of the support strip 3 moves, the tightening portions 31 to 34 moves in conjunction with one another following the movement, thereby compressing the other body parts and massaging the surrounding muscles, blood vessels and nerves, resulting in promotion of the flow of blood and lymph.

Furthermore, in the compression sock 1 according to the present embodiment, an upper end portion of the body portion 2 is formed so as to reach a position covering the lower end 111 of the knee cap. Covering a knee provides a heat-retention effect comparable to that obtained when a dorsal neck is covered. Accordingly, blood circulation can be further improved, enabling removal of cold in the toes.

Although the present invention has been described in details based on an embodiment thereof, the present invention is not limited to the above-described embodiment. Although in the embodiment, a leg garment according to the present invention has been described taking the compression sock 1 as an example, a leg garment according to the present invention can be applied to other products such as socks, leg supports, stockings and tights, in addition to knee-high socks.

Furthermore, although in the above-described embodiment, the support strip 3 is provided by changing the knitting texture from that of a portion around the support strip 3, thereby producing a tightening force larger than that of the portion around the support strip 3, the tightening portion may be configured by another method. For example, the support strip may be formed using a patch. Also, the support strip may be formed by fusing a resin to the fabric of the body portion.

Different tightening forces may be provided by providing the support strip 3 with different widths. Also, the texture may arbitrarily be changed within the respective tightening portions 31 to 34.

Although in the above-described embodiment, the position from which the support strip 3 starts is a position of the plantar part corresponding to the body of the third or fourth metatarsal bone, the support strip 3 may be formed starting from the arch, for example.

Although in the above-described embodiment, the compression sock 1 is formed so as to cover the toes, the compression sock 1 may be an open toe-type compression sock not covering the toes.

Although in the above-described embodiment, the support strip 3 is formed so as to reach the ventral aspect of the lower end of the knee cap, the support strip 3 may not necessarily be formed so as to reach the ventral aspect of the lower end of the knee cap. For example, the compression may be a short one having a length terminating at the upper part of the Achilles tendon.

Although in the above-described embodiment, the compression sock 1 include one continuous support strip 3, a plurality of support strips 3 may be provided in parallel. Alternatively, the compression sock 1 may be one including support strips 3 that are not continuous with one another.

A compression sock 1 according to an embodiment of the present invention, which is illustrated in FIG. 1, was manufactured as an example, and was evaluated as follows. Each of compression socks according to comparative examples 1 and 2 is one provided with hoop tension that gradually decreases from an ankle to a calf, without a support strip 3 having an inwardly-wound helical shape. The number of stitches in the compression sock according to example 1 was 144, that of the compression sock according to comparative example 1 was 240, and that of the compression sock according to comparative example 2 was 240. The size of the respective compression socks was 23-25 cm. In FIGS. 12 to 15, which illustrate the results of the evaluation, "B" denotes a bare foot, "$S_1$" denotes comparative example 1, "$S_2$" denotes comparative example 2, and "$S_0$" denotes example 1.

(Tensile test) A tensile test was conducted for arbitrary measurement sites of each of the compression socks according to example 1 and comparative examples 1 and 2, and the resulting dimension (tensile dimension) of each of the socks was measured. A test was started with a distance between chucks of 50 mm for each of measurement sites L11 to L16, and the length of each of the measurement sites was recorded with a maximum load of 3.5 kgf imposed thereon. Then, the distance between chucks of 50 mm was added to the actual measurement value, and the resulting value was recorded as a tensile dimension.

Test Conditions

Figure 10:
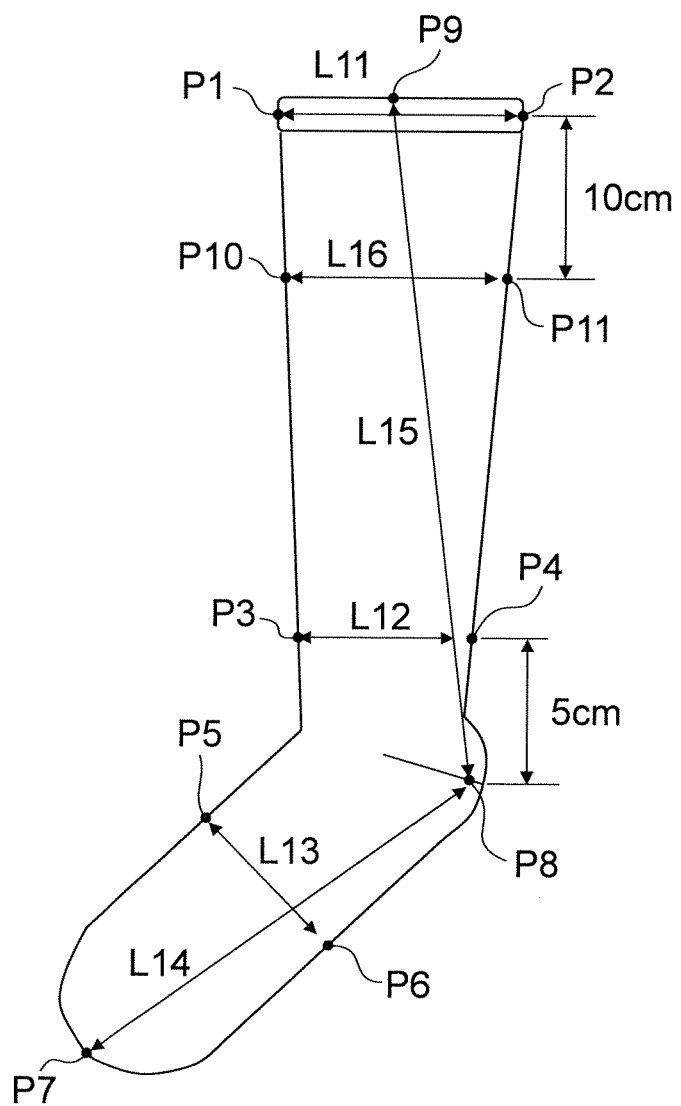
FIG. 10 is a diagram illustrating parts measured in a tensile test.

Tester: Tensile tester (AUTOGRAPH AGS-H 50N (manufactured by Shimadzu Corporation))
Test environment: temperature of 20° C. and relative humidity of 65% (constant temperature and humidity room)
Test speed: 300 mm/min
Maximum load: 3.5 kgf (=34.3 N)
Grip width: 10 mm
Grip margin: 10 mm FIG. 10 is a diagram illustrating respective measurement sites of the compression socks according to example 1 and comparative examples 1 and 2. Table 1 indicates tensile dimension values of the compression socks according to example 1 and the comparative examples 1 and 2.

A cuff breadth L11 is a measurement site between a ventral point P1 and a dorsal point P2 along a straight line connecting the two points of a cuff formed at an upper end portion of the compression sock. An ankle breadth L12 is a position corresponding to an ankle of a wearer, and is a measurement site between a ventral point P3 and a dorsal point P4 along a straight line connecting the two points of a site five centimeters from the heel.

A foot breadth L13 is a value of a position corresponding to an instep and an arch of a wearer, and is a measurement site between an instep-side point P5 and an arch-side point P6, which are middle points between the gore line of the heel and the toes along a straight line connecting the two points. A foot breadth L14 is a measurement site between a point P7 corresponding to the toes and a point P8 corresponding to the heel along a straight line connecting the two points.

A total length stretch L15 is an tensile dimension between a point P9, which is a middle point in the anterior-posterior direction of an upper end portion of the compression sock, and a point P8 corresponding to the heel along a straight line connecting the two points. A calf breadth L16 is a tensile dimension between a ventral point P10 and a dorsal point P11 in a site ten centimeters below the upper end portion of the compression sock along a straight line connecting the two points.

TABLE 1

| | | Tensile dimension (mm) | | | Average Value | sd |
|---|---|---|---|---|---|---|
| Cuff breadth L11 | Example 1 | 224.69 | 225.75 | 225.75 | 225.58 | 0.67 |
| | Comparative example 1 | 209.73 | 211.09 | 212.19 | 211.00 | 1.01 |
| | Comparative example 2 | 245.07 | 246.58 | 247.57 | 246.41 | 1.03 |
| Ankle breadth L12 | Example 1 | 166.65 | 167.55 | 168.15 | 167.45 | 0.62 |
| | Comparative example 1 | 152.63 | 153.47 | 154.07 | 153.39 | 0.59 |
| | Comparative example 2 | 171.81 | 174.52 | 175.62 | 173.98 | 1.60 |
| Foot breadth L13 | Example 1 | 144.4 | 145.05 | 145.55 | 145.00 | 0.47 |
| | Comparative example 1 | 146.62 | 147.6 | 148.26 | 147.49 | 0.67 |
| | Comparative example 2 | 177.63 | 179.12 | 179.12 | 178.87 | 0.93 |
| Foot stretch L14 | Example 1 | 268.23 | 268.87 | 269.22 | 268.77 | 0.41 |
| | Comparative example 1 | 281.8 | 283.31 | 284.21 | 283.11 | 0.99 |
| | Comparative example 2 | 286.2 | 287.67 | 288.37 | 287.41 | 0.90 |
| Total length stretch L15 | Example 1 | 624.63 | 624.56 | 624.79 | 624.66 | 0.10 |
| | Comparative example 1 | 550.93 | 553.73 | 555.03 | 553.23 | 1.71 |
| | Comparative example 2 | 544.92 | 546.56 | 547.81 | 546.43 | 1.18 |
| Calf breadth L16 | Example 1 | 207.92 | 209.02 | 209.92 | 208.95 | 0.82 |
| | Comparative example 1 | 192.89 | 194.09 | 194.65 | 193.88 | 0.73 |
| | Comparative example 2 | 227.25 | 229.01 | 230.47 | 228.91 | 1.32 |

Figure 11:
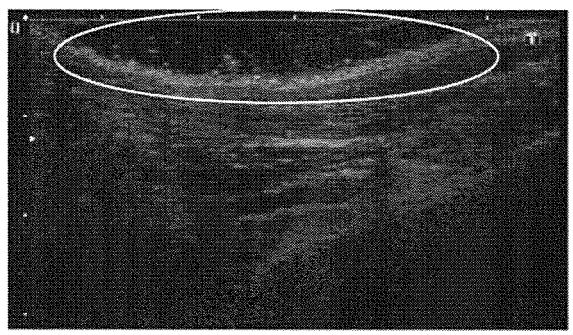
FIGS. 11(A), 11(B) and 11(C) are diagrams each illustrating an echogram, which is a result of an ultrasound echographic test.
Figure 11:
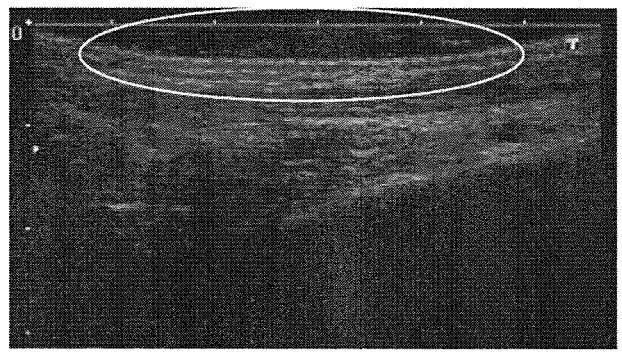
Figure 11:
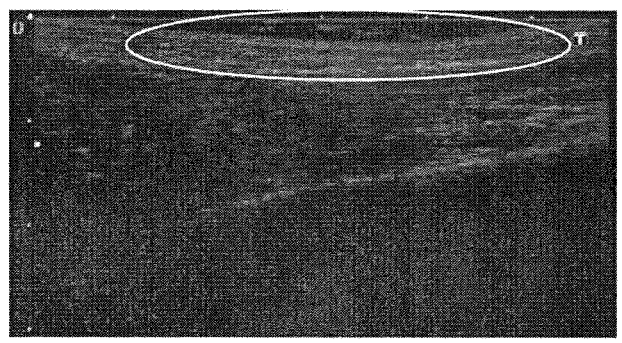

(Ultrasound echographic test) Next, an ultrasound echographic test was conducted for each of the compression socks according to example 1 and comparative examples 1 and 2. FIGS. 11(A) to 11(C) each illustrate an echogram that is a result of the ultrasound echographic test. FIG. 11(A) is an echogram after the compression sock according to comparative example 1 was worn. FIG. 11(B) is an echogram after the compression sock according to comparative example 2 was worn. FIG. 11(C) is an echogram after the compression sock according to example 1 was worn.

An ultrasound echographic test was conducted for a ventral ankle of a same subject, and the echograms illustrated in FIGS. 11(A) to FIG. 11(C) were obtained. The subject started wearing the respective compression sock at 8:00 a.m. and put the compression sock off at 0:00 p.m., which is four hours later. Then, the echograms, which are results of the test, were taken for the leg in a bared state.

According to the echograms illustrated in FIGS. 11(A) and 11(B), the leg did not recover from a dent even after putting the sock off in comparative examples 1 and 2. Meanwhile, in example 1, it can be seen that the leg recovered from a dent. Consequently, in example 1, the subcutaneous tissue was less damaged.

Figure 12:
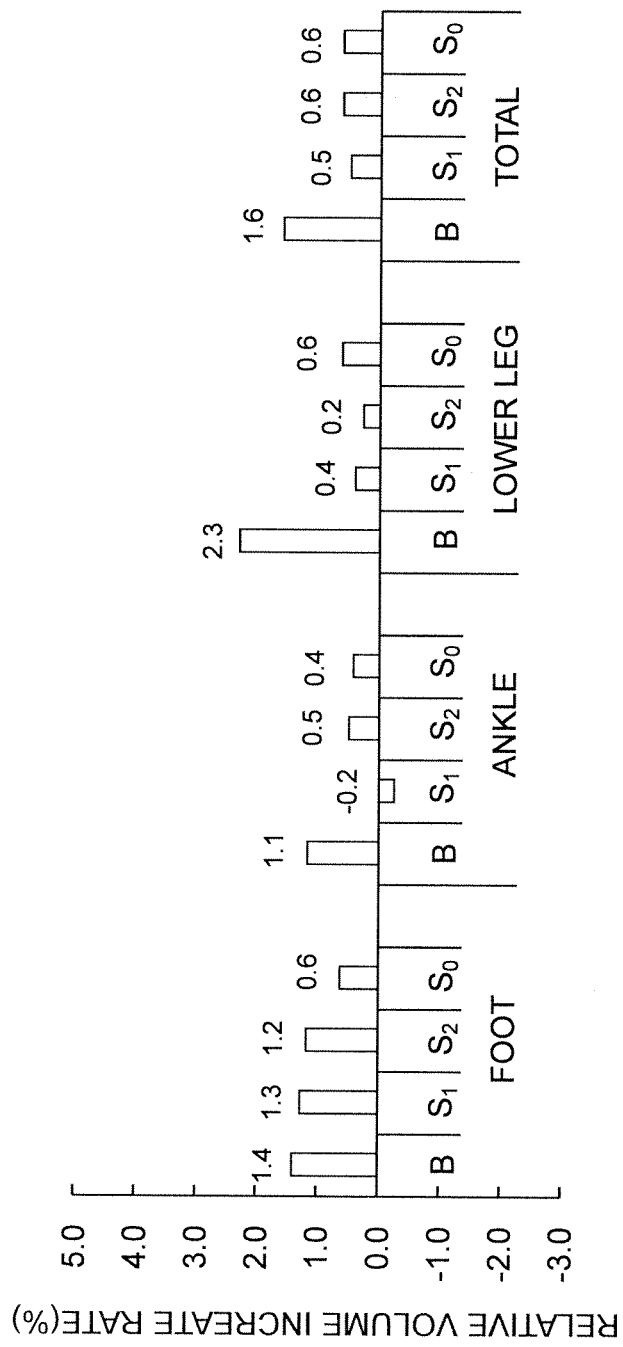
FIG. 12 is a graph illustrating relative volume increase rates (%)

(Lower leg and foot volume change confirmation test) Next, a test for confirming volume change of a lower leg and a foot of a wearer was conducted for each of the compression socks according to example 1 and comparative examples 1 and 2. FIG. 12 is a graph illustrating relative volume increase rates (%). The volumes of a lower leg and a foot of each of seven subjects in their early twenties was measured in the morning, and then the subjects each more the respective compression sock and the volumes were measured four hours later. FIG. 12 illustrates increase rates of the volumes with the volumes in the morning as 100%. A bar denoted by B in FIG. 12 indicates a volume increase rate in the case of a bared foot. A bar denoted by $S_1$ in FIG. 12 indicates a volume increase rate where the compression sock according to comparative example 1 was worn. A bar denoted in $S_2$ in FIG. 12 indicates a volume increase rate where the compression sock according to comparative example 2 was worn. A bar denoted by $S_0$ in FIG. 12 illustrates a volume increase rate where the compression sock according to example 1 was worn (the same applies to FIGS. 13, 14 and 15). The measurement results illustrated in FIG. 12 shows that any of the socks according to example 1 and comparative examples 1 and 2 have a significantly reduced volume compared to the bare foot, and thus, have a swelling removal effect.

Figure 13:
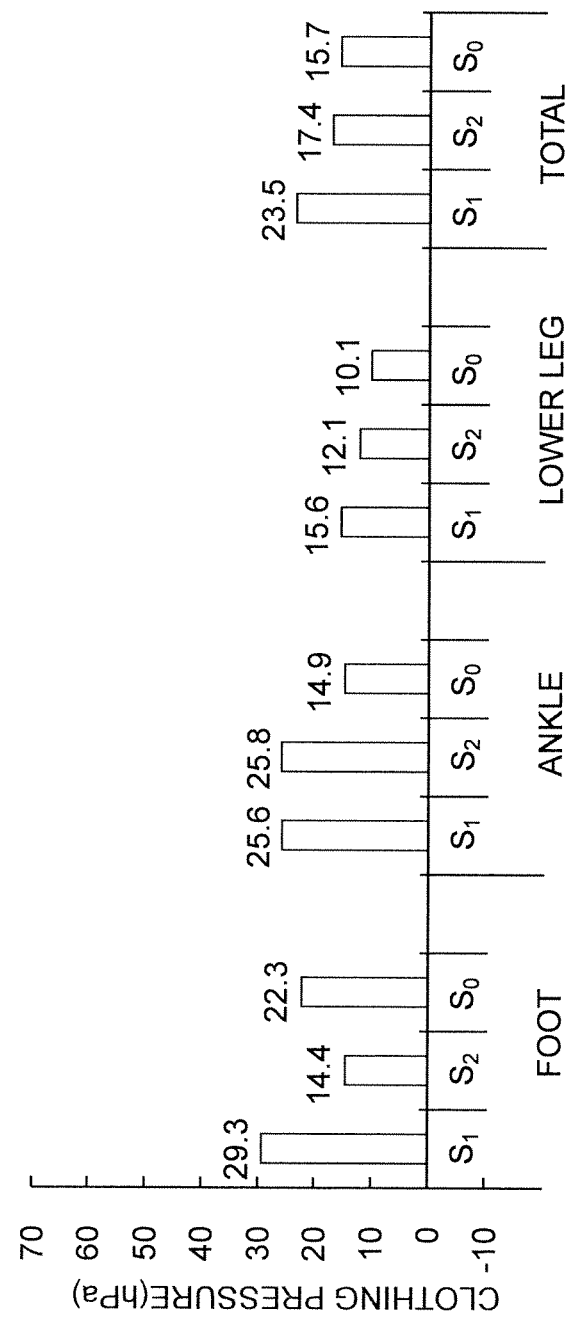
FIG. 13 is a graph illustrating clothing pressure measurement results.

(Clothing pressure measurement) Next, closing pressure measurements were conducted for each of the compression socks according to example 1 and comparative examples 1 and 2 when they are worn. FIG. 13 is a graph illustrating the results of the closing pressure measurements. Sites to be measured in the closing pressure measurements were a total of 19 points including four points in a cuff, four points in a maximum lower leg circumference, four points in an ankle circumference, three points in an arch, three points in a toe, and one point in a heel. As illustrated in FIG. 13, although example 1 exhibits 22.3 hPa for the foot, which causes no problem even where it is tightened, in the total evaluation representing an average value of the values for the foot, the ankle and the lower leg, example 1 exhibits the smallest closing pressure. In other words, it can be seen that in example 1, swelling can be reduced even with a relatively small tightening force.

Figure 14:
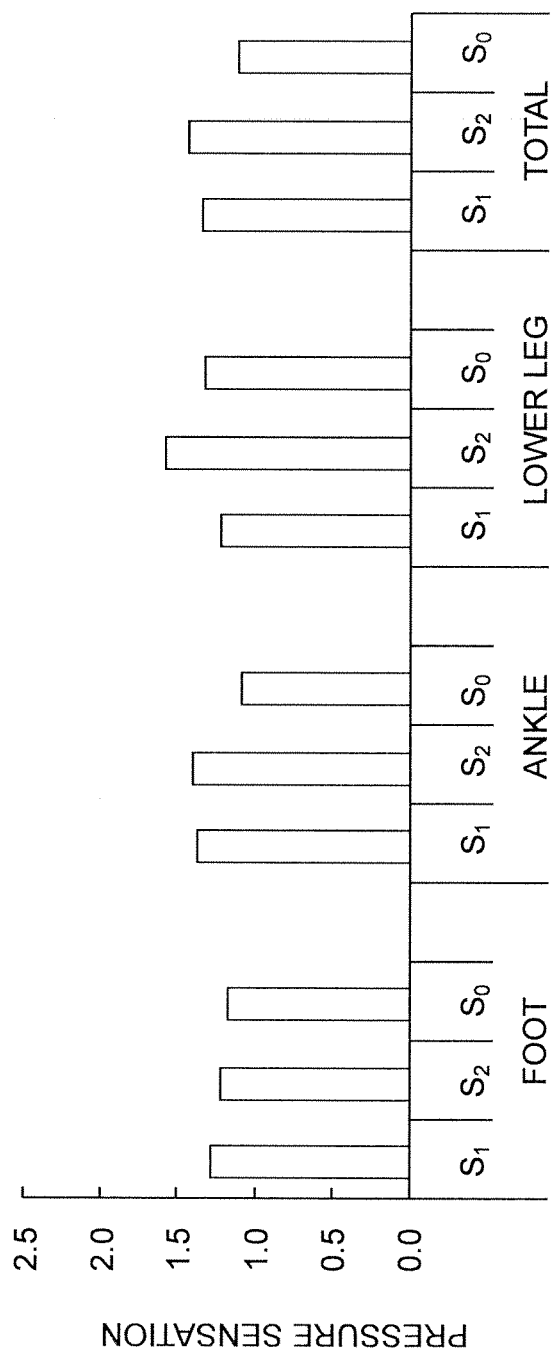
FIG. 14 is a graph illustrating pressure sensation measurement results.

(Pressure sensation measurements) Next, pressure sensations for each of the compression socks according to example 1 and comparative examples 1 and 2 when they are worn were measured using a ratio scale. FIG. 14 illustrates a graph indicating the results of the pressure sensation measurements. Subjects were made to evaluate the degrees of pressure sensations (sensations of tightness) for the compression socks according to example 1 and comparative examples 1 and 2 when the subjects wore the compression socks. First, the subjects were repeatedly provided with pressure simulations using a band so as to have a feeling of moderateness as a pressure sensation for a standard strength and so as to have a feeling of considerable tightness as a pressure sensation for a strength larger than the standard strength to recognize the magnitudes of the respective sensations. Here, a questionnaire sheet including a straight line was given to each of the subjects to make the subjects recognize the pressure sensations as positions in a line segment. For example, one end of the line segment was determined as a position of "moderate". A point a certain distance away from the one end was determined as a position of "considerably tight".

Next, the subjects were made to wear the compression socks, and instructed to express the pressure sensation of that time by putting an arrow on the line segment on the questionnaire. Then, setting "moderate" to be "1.0" and "considerably tight" to be "10.0", the lengths from "moderate" to the put arrows were measured and quantified. Here, the value of the pressure sensation for the subjects to have a feeling of "loose" was "0.5", and the value of the pressure sensation for the subjects to have a feeling of "tight" was "2.3". From the results, it was confirmed that example 1 provided lowest pressure sensations compared to those in comparative examples 1 and 2, and very close to "1.0" in which the subjects have a feeling of "moderate". Here, the subjects are seven women in their early twenties, and FIG. 14 illustrates average values of the subjects.

Figure 15:
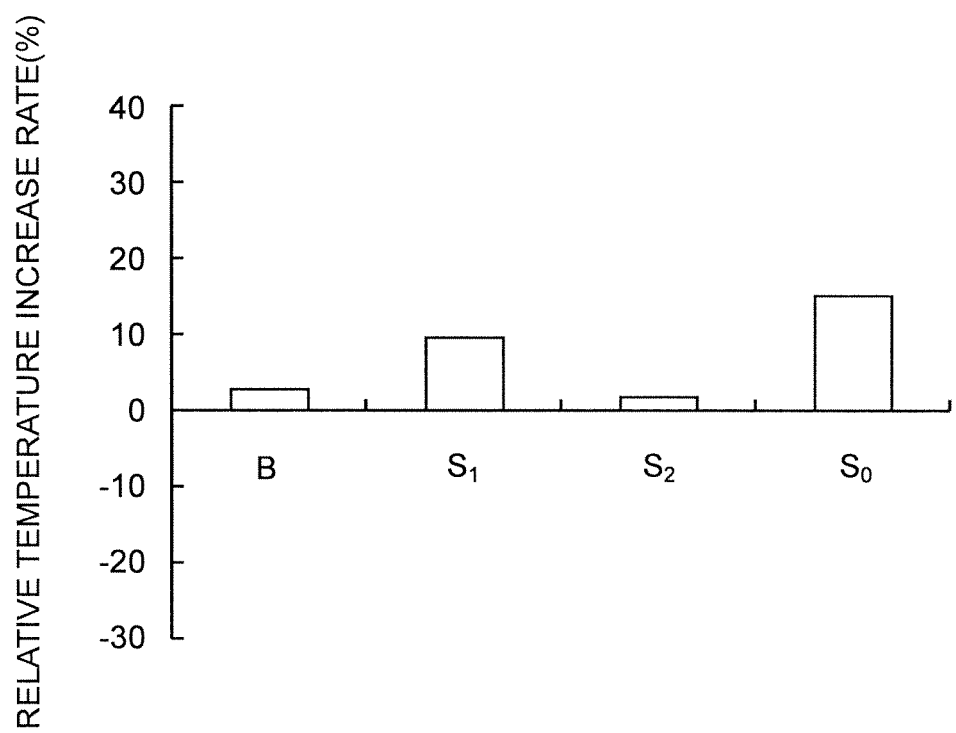
FIG. 15 is a graph illustrating relative temperature increase rates (%).

(Skin temperature measurements) Next, a skin temperature change was measured for each of the compression socks according to example 1 and comparative examples 1 and 2 when they are worn. A skin temperature of the ten toes of each of subjects was measured in the morning, the subjects each wore the respective compression sock and a temperature of the skin of the toes was measured again four hours later. FIG. 15 is a graph illustrating relative temperature increase rates. FIG. 15 illustrates the measurement values after the elapse of four hours with reference to the measurement values in the morning as 100%. The subjects were seven women in their early twenties. FIG. 15 indicates average values of the subjects. From the test results, it was confirmed that the skin temperature after wearing the sock according to example 1 is most favorable compared to the measurements results for the bared foot and the compression socks according comparative examples 1 and 2.

With the compression sock 1 according to example 1, swelling was removed effectively with lowered compression values. Furthermore, it was confirmed that the volumes of the foot and the lower leg were significantly reduced.

In other words, with the compression sock according to example 1, a wearer wore the sock without bearing excessive compression, the blood circulation was promoted because of the heat-retention effect the compression sock has as a knee-high sock, and swelling was removed. Furthermore, with the compression sock 1 according to example 1, which enables maintenance of good blood circulation in the toes, the toes were warmed up. Furthermore, with compression sock 1 according to example 1, swelling in the leg was removed and tiredness of the leg was reduced.

As described above, with a leg garment according to an embodiment of the present invention in which an inwardly-wound helical support strip is formed to compress a ventral ankle via a surface thereof, the support strip being arranged so as to medially extend from an instep to a sole of a foot, blood circulation is promoted to remove swelling while optimizing pressure sensation, as well as suppressing occurrence of impediments for blood circulation to maintain a heat-retention effect. Consequently, it is possible to prevent a wearer from having a discomfort feeling of "too tight" and also prevent a decrease in temperature of the skin of the foot.

What is claimed is:

1. A leg garment configured for covering at least an instep, a sole and an ankle of a leg, the leg garment comprising:
    a body portion comprising stretchable, knitted fabric material; and
    a support strip arranged in the shape of an inwardly-wound helix extending from the instep to the ankle through the sole, the support strip exerting a tightening force larger than that of a portion of the stretchable, knitted fabric material around the support strip,
wherein the support strip includes:
a first tightening portion arranged so as to medially extend from the instep to the sole; and
a second tightening portion arranged so as to extend obliquely upward from a lateral side to a medial side of a ventral ankle, the second tightening portion compressing the ventral ankle via a surface thereof,
wherein the support strip includes an edge that extends continuously from the first tightening portion to the second tightening portion, and the edge forms a helix that runs from the first tightening portion to the second tightening portion,
the support strip further includes a third tightening portion arranged so as to cover a portion of the leg above an Achilles tendon,
wherein the stretchable, knitted fabric material of the body portion is configured to cover a lower part of the Achilles tendon, an area of the stretchable, knitted fabric material of the body portion defining interval distances between portions of the support strip, the interval distances being non-uniform;
the interval distance between the first tightening portion and the second tightening portion at a front region of the leg garment is less than the interval distance between the first tightening portion and the third tightening portion at a rear region of the leg garment, and
at a side region of the leg garment between the front region and the rear region, the interval distance between the first tightening portion and the second tightening portion is less than the interval distance between the first tightening portion and the third tightening portion.

2. The leg garment according to claim 1, wherein the body portion is formed so as to cover at least a part up to a part of the leg above the ankle; and
wherein the third tightening portion is arranged so as to cover a muscle-tendon junction connecting the Achilles tendon and a triceps surae muscle, and a lower end side of the third tightening portion is continuous with an upper end side of the second tightening portion.

3. The leg garment according to claim 1 or 2, wherein the body portion is formed so as to cover at least a part of the leg up to a lower leg; and
wherein the support strip includes a fourth tightening portion arranged so as to extend obliquely upward from an external side of the lower leg to a ventral side of the lower leg to reach a ventral side of a lower end of a knee cap.

4. The leg garment according to claim 2, wherein the edge of the support strip extends continuously from the second tightening portion to the third tightening portion, and the helix formed by the edge runs from the first tightening portion to the third tightening portion.

5. The leg garment according to claim 1, wherein the body portion is formed so as to cover at least a part of the leg from a position corresponding to a body of a metatarsal bone to a position corresponding to the lower end of the knee cap;
wherein the support strip is formed so as to continuously extend from a position in a plantar part corresponding to a body of a third or fourth metatarsal bone to a position corresponding to the ventral side of the lower end of the knee cap; and
wherein values of pressures exerted by the body portion satisfy expression below:

foot circumference:minimum lower leg circumference:maximum lower leg circumference=2.2: 1.6:1.0.

6. The leg garment according to claim 1, wherein the support strip has a first end and a second end, the first tightening portion begins at the first end, and the first end is located at the sole.

7. The leg garment according to claim 1, wherein the support strip is integral with the stretchable, knitted fabric material of the body portion.

* * * * *